US005741305A

United States Patent [19]
Vincent et al.

[11] Patent Number: 5,741,305
[45] Date of Patent: Apr. 21, 1998

[54] KEYED SELF-LATCHING BATTERY PACK FOR A PORTABLE DEFIBRILLATOR

[75] Inventors: Stephen T. Vincent, Redmond; Shawn R. Bertagnole, Seattle; Richard J. Cardin, Duvall, all of Wash.

[73] Assignee: Physio-Control Corporation, Redmond, Wash.

[21] Appl. No.: 643,467

[22] Filed: May 6, 1996

[51] Int. Cl.⁶ .......................................................... A61N 1/39
[52] U.S. Cl. ................................................. 607/5; 439/500
[58] Field of Search ............................ 439/500, 928.1; 607/5

[56] References Cited

U.S. PATENT DOCUMENTS

| | | |
|---|---|---|
| 5,224,870 | 7/1993 | Weaver et al. ................... 607/5 |
| 5,350,317 | 9/1994 | Weaver et al. ................ 439/500 |
| 5,470,343 | 11/1995 | Fincke et al. ..................... 607/5 |

Primary Examiner—William E. Kamm
Assistant Examiner—Scott M. Getzow
Attorney, Agent, or Firm—Christensen O'Connor Johnson & Kindness PLLC

[57] ABSTRACT

A battery pack (28) for a portable defibrillator (30). The battery pack has a latch (34) that is biased in an extended position. When the battery pack is inserted into a battery well (30) in the portable defibrillator, the latch automatically latches into a slot (124) to secure the battery pack in the battery well. Ridges (112) are provided on the floor (108) of the battery well to reduce the friction between the battery pack and the floor of the well as the battery pack is inserted into the defibrillator. A ridge (38) is also provided around the periphery of the top (36) of the battery pack to reduce the friction between the battery pack and the ceiling of the battery well. A right wall (44) of the battery pack is inclined from vertical so that a cross section of the battery pack is trapezoid in shape. The asymmetric cross-section prevents the battery pack from being incorrectly inserted into the battery well. The disclosed battery pack construction simplifies the replacement of the battery pack in the portable defibrillator.

4 Claims, 7 Drawing Sheets

KEYED SELF-LATCHING BATTERY PACK FOR A PORTABLE DEFIBRILLATOR

FIELD OF THE INVENTION

The invention generally relates to power supplies for portable defibrillators, and more specifically to battery packs for portable defibrillators.

BACKGROUND OF THE INVENTION

The probability of surviving a heart attack depends on the speed with which appropriate medical care is provided to the person experiencing the heart attack. To decrease the response time to a patient suffering a heart attack, it has been recognized that those persons who are typically first to arrive at the scene of a medical emergency, including emergency medical technicians (EMTs), firefighters, the police, and even the public (hereinafter collectively referred to as "first responders") should be provided with portable defibrillators. A first responder equipped with a portable defibrillator will have a greater likelihood of successfully treating the patient than those who arrive later at the scene. A defibrillator designed for first responder use would therefore improve the overall success rate of treating heart attack patients.

Unlike paramedics and other trained medical personnel, however, first responders will typically not have received extensive training on dealing with medical emergencies. Because of the reduced level of expertise in the first responder group, a portable defibrillator provided to the first responders should be as simple and user friendly as possible. Reducing the complexity of the portable defibrillator ensures that even in stressful emergency situations, the first responder would be able to connect the defibrillator to the patient and apply appropriate therapy.

All defibrillators must contain or be connected to an energy source to generate and apply a defibrillation pulse to the patient. To ensure true portability, most portable defibrillators are constructed with a battery pack that is sufficient to operate the portable defibrillator for a period of time. The battery pack may be either rechargeable or non-rechargeable, depending on the user's preference and the environment in which the defibrillator is to be used. Rechargeable battery packs typically power a defibrillator for a shorter period of time than non-rechargeable battery packs, but can be recharged and reused. In contrast, non-rechargeable battery packs allow the defibrillator to operate for a longer period but require replacement when the battery pack is discharged.

A portable defibrillator is unusable as a medical treatment device without the battery pack or with a battery pack that is discharged. It should therefore be very easy for the first responder to remove and replace the battery pack to ensure that the defibrillator is always available for use. In most situations, changing the battery pack will typically occur during normal testing of the defibrillator in a non-emergency setting. Occasionally, however, a first responder may have to change the battery pack at the site of the emergency. For example, a prior user of the defibrillator may have left a discharged battery pack in the device that is not discovered until treatment is to be initiated on a patient. Alternatively, the defibrillator could be in use when the battery pack becomes discharged, requiring the first responder to replace the battery pack before continuing treatment. To speed the changing of battery packs, it would therefore be desirable to make the changing process as simple and intuitive as possible.

Unfortunately, the replacement of many prior art battery packs in portable defibrillators was not very straightforward. For example, the correct orientation to insert the battery pack into the portable defibrillator was often not readily apparent from the shape of the battery pack. Further, the connection scheme to connect the battery pack to the defibrillator often required a precise alignment of conductive pins in the battery pack and sockets in the defibrillator. If the pins were not aligned as the battery pack was being inserted into the defibrillator, the user ran the risk of bending and/or breaking the pins. Moreover, prior art battery packs often did not easily latch into the defibrillator. Without a positive and simple latching mechanism to secure the battery pack to the portable defibrillator, a user had to be careful when installing the battery pack to ensure that it was appropriately attached to the device. All of the above disadvantages of prior art battery combined to make it a difficult operation to replace a battery pack in a portable defibrillator, a task that usually required a user to use both hands when performing the replacement.

The present invention is directed to overcoming the foregoing and other disadvantages. More specifically, the present invention is directed to an improved battery pack design that may be easily inserted by a first responder into a portable defibrillator.

SUMMARY OF THE INVENTION

A keyed self-latching battery pack for a portable defibrillator is disclosed. The battery pack has several features that simplify the insertion of the battery pack into the portable defibrillator. In accordance with one aspect of the invention, the case of the battery pack is shaped to prevent the battery pack from being inserted backwards or upside-down into a battery well within the defibrillator. Preferably, one of the sides of the battery pack is inclined at an angle to the opposing side, so that a cross-section of the battery pack is trapezoidal in shape. Keying the battery pack in this manner ensures that the battery pack is properly inserted into the portable defibrillator.

In accordance with another aspect of the invention, a self-latching latch is provided on the battery pack. The self-latching latch has an angled leading face so that as the battery pack is inserted into the defibrillator, the latch is automatically moved to a retracted position. When the battery pack is fully inserted into the defibrillator and the latch is located adjacent a corresponding slot, biasing means within the latch bias the latch into an extended position. In the extended position, a portion of the latch extends into the slot to ensure that the battery pack cannot accidentally be separated from the unit, e.g., when the defibrillator is dropped. Removing the battery pack requires manually moving the latch to the retracted position in order to retract the latch from the slot and allow the battery pack to be withdrawn from the battery well.

In accordance with still another aspect of the invention, friction-reducing ridges are formed on the surface of the battery pack and within the battery well. The ridges protrude from the surface of the battery pack, and protrude from the walls of the battery well. As the battery pack is inserted into the defibrillator, the battery pack slides on the ridges rather than on the smooth interior walls of the battery well. The ridges prevent the battery pack from becoming jammed in the defibrillator due to dirt, debris, or liquids that may accidentally accumulate in the battery well.

In accordance with yet another aspect of the invention, guides are constructed within the battery well to ensure that the battery pack is correctly aligned as it is inserted into the defibrillator. Conductive pins in the battery pack are therefore automatically aligned with corresponding conductive sockets in the defibrillator as the battery pack is inserted into the defibrillator. Since the battery pack is automatically aligned, a user does not have to be concerned with damaging or breaking the pins on the battery pack when the battery pack is inserted into the defibrillator.

In accordance with still another aspect of the invention, the conductive pins in the battery pack are located on the back of the battery pack case, opposite the latch on the front of the battery pack. Locating the conductive pins and latch on opposing ends of the battery pack minimizes the chance that a user would inadvertently come in contact with the pins as the battery pack is being installed. The location of the conductive pins on the battery pack also dictates locating the corresponding conductive sockets in the defibrillator on the rear wall of the battery well. The user is therefore also prevented from contacting the conductive sockets in the defibrillator.

Several advantages arise from the battery pack construction disclosed herein. The keying system ensures that the battery pack is correctly oriented when inserted into the portable defibrillator. The guides and friction reducing ridges ensure that the insertion of the battery is smooth and accurate. Once inserted, the self-latching mechanism ensures that the battery pack is not accidentally separated from the portable defibrillator. A relatively untrained first responder can therefore easily replace the defibrillator battery pack with minimal effort and without extensive training. The battery pack construction disclosed herein simplifies the operation of the defibrillator and makes the defibrillator accessible to a larger group of users.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
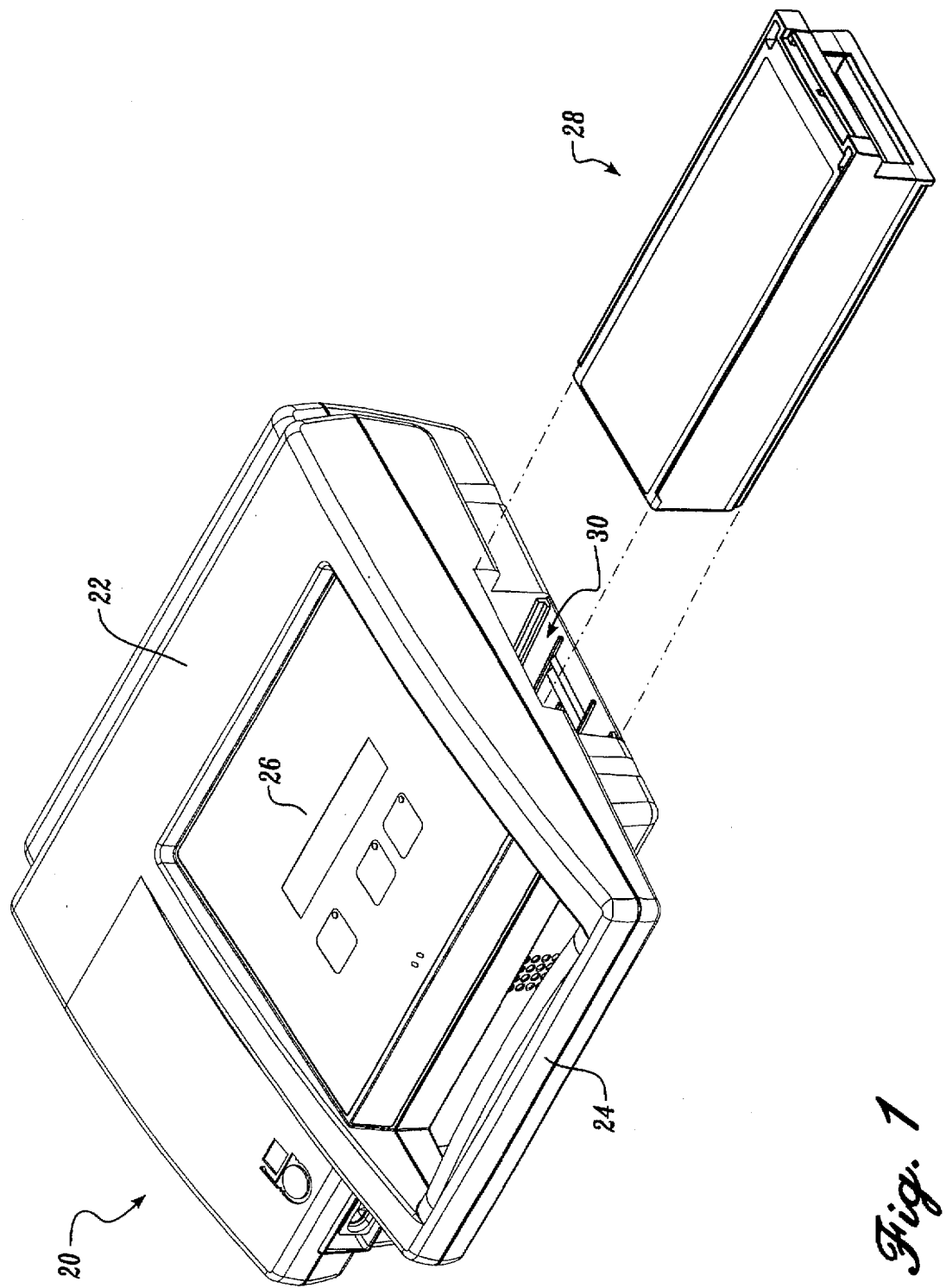
FIG. 1 is a perspective view of a portable defibrillator and a battery pack formed in accordance with the present invention.

FIG. 1 depicts a portable defibrillator 20 designed for use by a first responder during a medical emergency. The particular defibrillator shown in FIG. 1 is a LIFEPAK® 500, manufactured and sold by Physio-Control Corporation of Redmond, Wash. To facilitate use in the field, defibrillator 20 is formed with an impact-resistant plastic case 22 having an integral handle 24 to allow the user to easily carry the defibrillator to a desired location. When used, the defibrillator is preferably positioned so that a control panel 26 on the defibrillator is oriented upwards towards the user. Control panel 26 contains a simplified interface that allows the user to operate the defibrillator after the defibrillator is connected to a patient. Appropriate keys are provided on the control panel to allow the user to turn the defibrillator on and off, to instruct the defibrillator to analyze the electrocardiogram (ECG) of the patient attached to the defibrillator, and to allow the user to apply a defibfillation pulse to the patient if the patient experiences a shockable heart rhythm.

Figure 2:
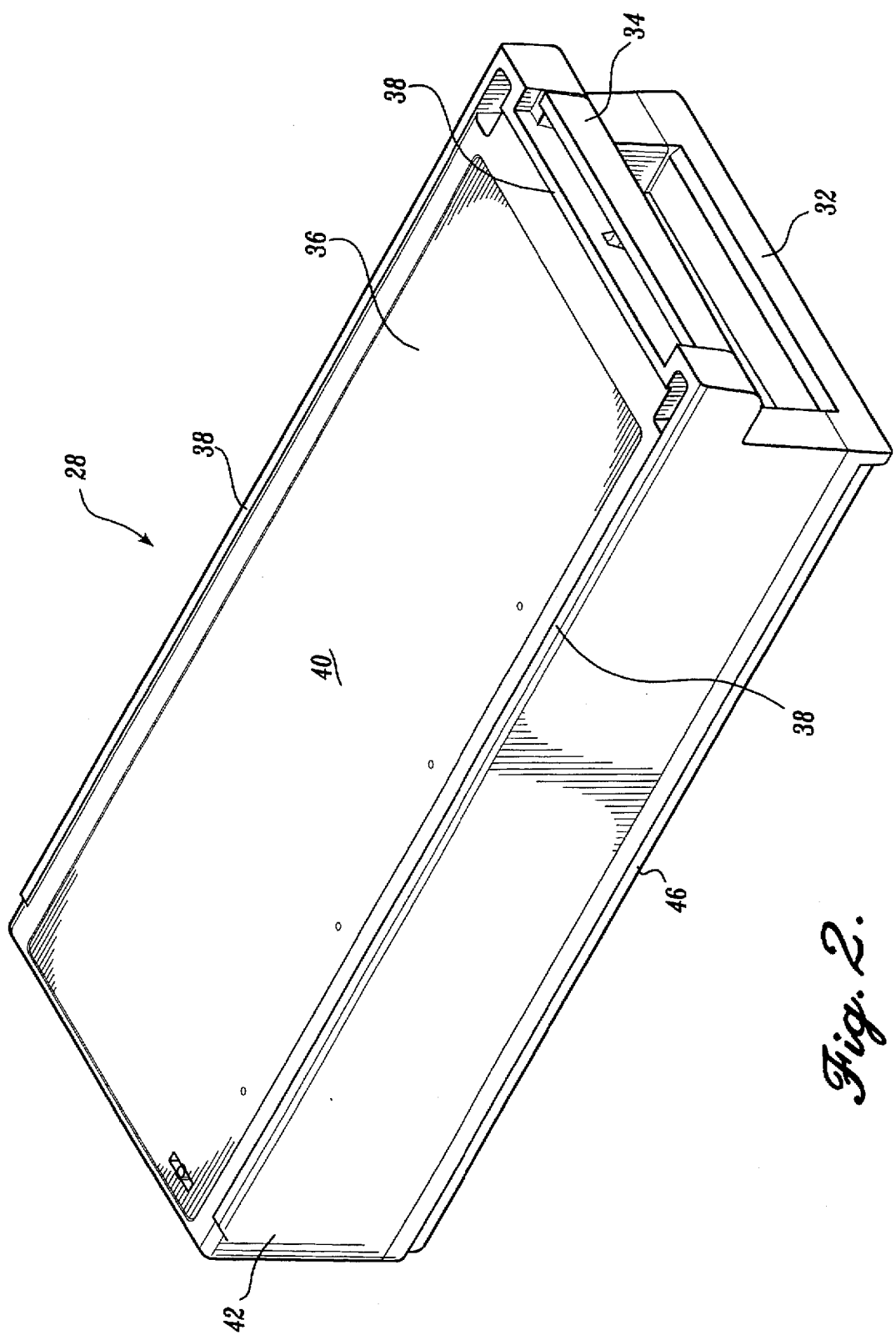
FIG. 2 is a perspective view of the battery pack showing a latch located on the front of the battery pack.
Figure 3:
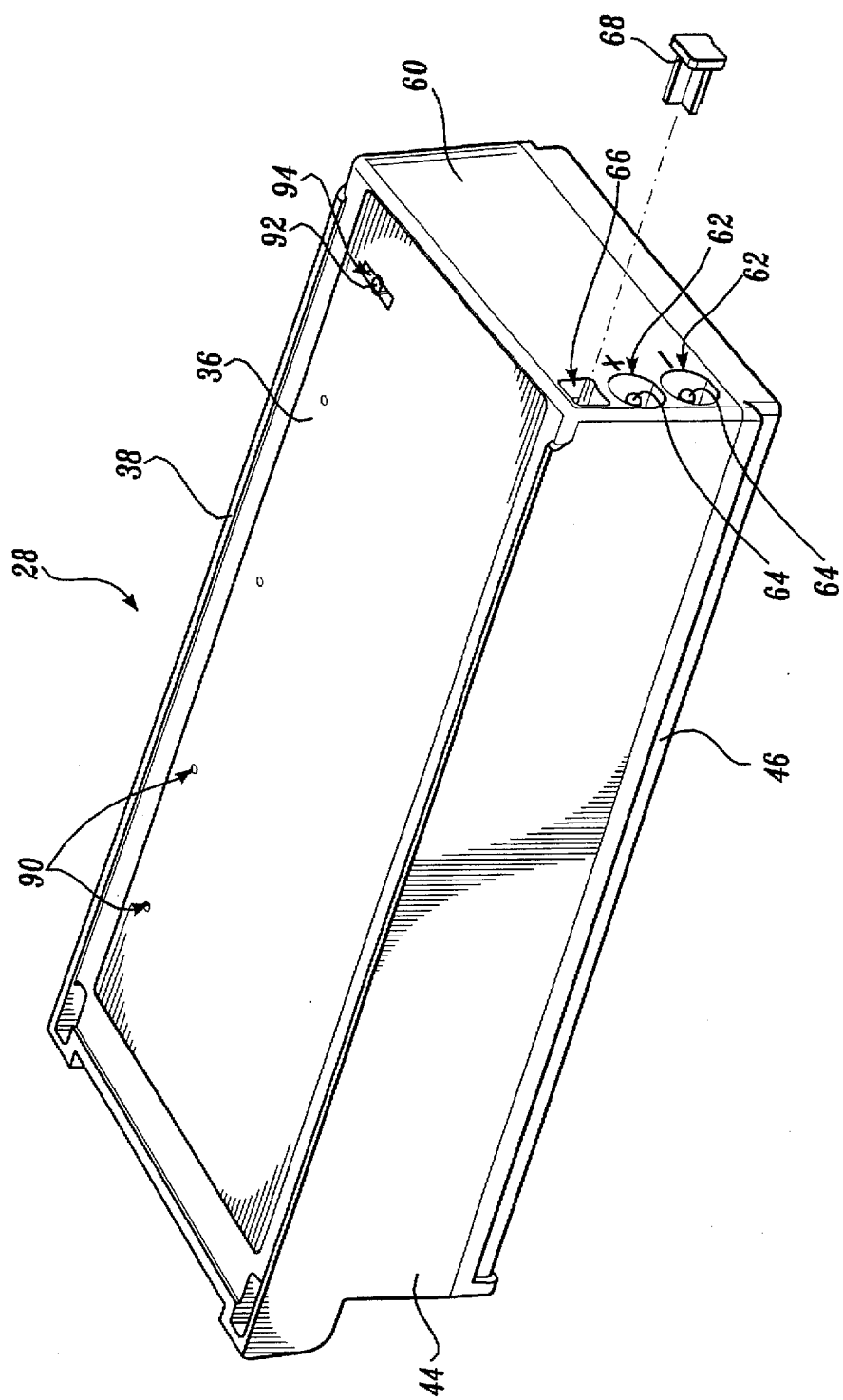
FIG. 3 is a perspective view of the battery pack showing a pair of conductive pins located on the back of the battery pack to electrically connect the battery pack to the portable defibrillator.

Power for the defibrillator is provided by a battery pack 28 that fits inside a battery well 30 located on the side of the defibrillator. As shown in the front and rear views of FIGS. 2 and 3, battery pack 28 is generally shaped like a shoe box having a front 32, back 60, top 36, bottom 54 and left and right sides 42, 44. The front 32 of the battery pack is formed with a latch 34 that extends across the majority of the front. The latch is grasped by a user to remove the battery pack from the defibrillator. As discussed in additional detail below, the latch automatically secures the battery pack in the battery well when the battery pack is inserted into the defibrillator. The front 32 of the battery pack is formed so that when the battery pack is inserted into the defibrillator, the front of the battery pack is flush with the case 22 of the defibrillator.

The top 36 of the battery pack is formed with a ridge 38 that protrudes above the top surface of the battery pack and extends around the periphery of the battery pack. The ridge 38 starts at the back of the battery pack, and extends along the left side, across the front, and along the right side of the battery pack. The ridge prevents the top of the battery pack from coming into direct contact with the walls in the battery well 30 as the battery pack is inserted into the defibrillator. The ridge therefore prevents the battery pack from jamming or otherwise getting stuck in the battery well due to the presence of debris or liquids. The top of the battery pack is also formed with a recessed region 40. The recessed region 40 allows a label to be affixed to the top of the battery pack without protruding above the ridge 38 around the periphery of the battery pack.

The left side 42 and right side 44 of the battery pack 28 are each formed with an in-cut corner 46 that extends along the bottom of the respective side for the length of the battery pack. As will be discussed below, corresponding guides are constructed in the battery well that fit within the corners 46. The guides ensure correct alignment of the battery pack as the battery pack is being inserted into the defibrillator.

To prevent incorrect insertion of the battery pack into the defibrillator, the left side 42 of the battery pack is not parallel with the right side 44 of the battery pack. As shown in the front view of FIG. 4, the left side 42 is generally vertical and the right side 44 is tipped at an angle $\alpha$ from vertical. A cross-section taken through the battery pack is therefore a trapezoid. Because the entrance of the battery well is the same shape as the battery pack cross-section, the battery pack cannot be incorrectly inserted into the battery well. That is, the battery pack cannot be inserted upside down, sideways, or with the latch facing the interior of the battery pack. Keying the battery pack with an asymmetric cross-section is especially advantageous in a first responder defibrillator, since it prevents the first responder from incorrectly inserting the battery pack into the defibrillator.

Figure 4:
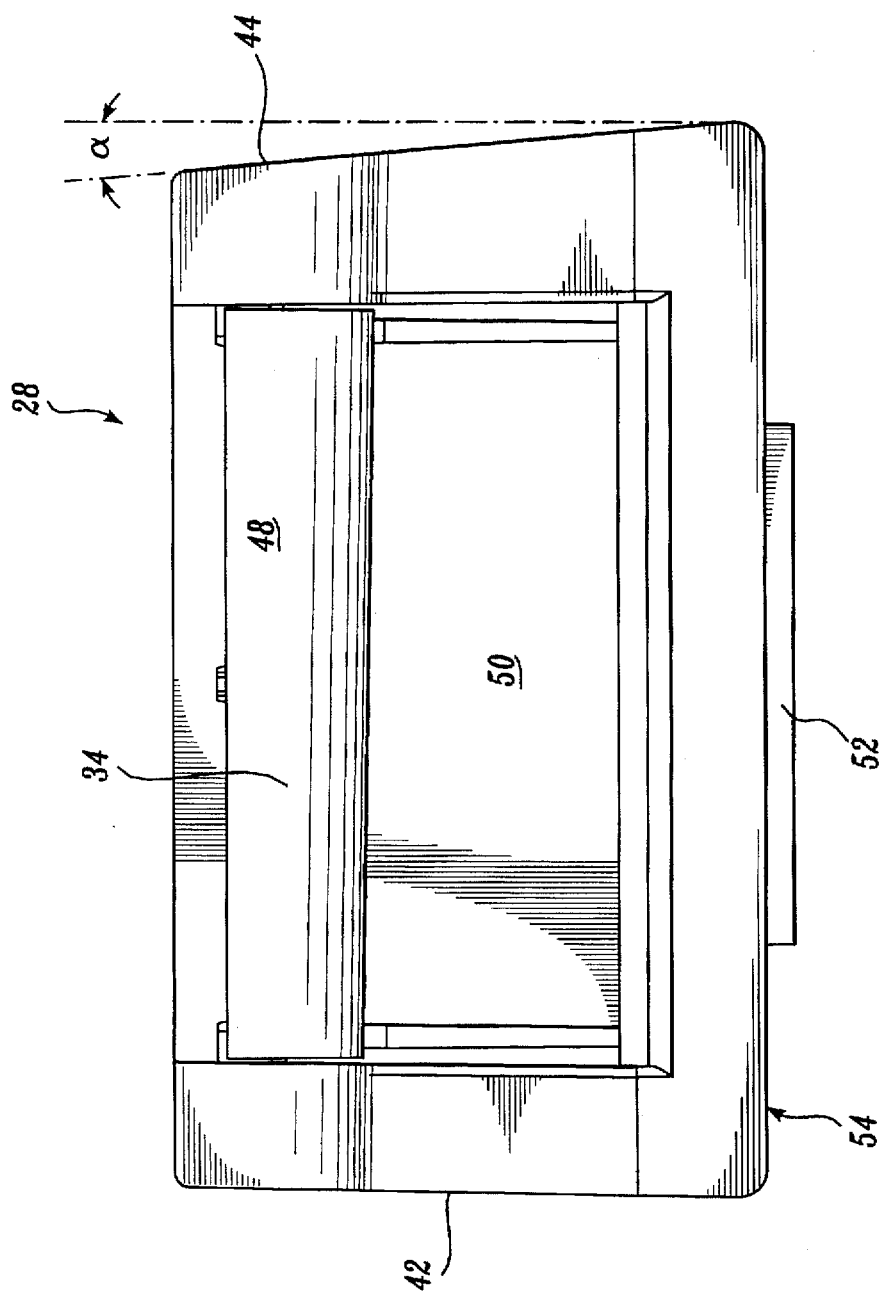
FIG. 4 is a front view of the battery pack showing a portion of the latch protruding from the bottom of the battery pack.

Also shown in FIG. 4 is a portion of the latch 34 construction. Latch 34 is molded as a single piece and includes a handle 48, a body 50, and a latch member 52. Latch member 52 protrudes below the bottom 54 of the battery pack when in an extended position. Upwards movement of the latch handle 48 causes a corresponding upwards movement of the latch member 52, raising the latch member above the bottom of the battery pack to a retracted position. As will be discussed below, movement of the latch allows the battery pack to be secured in the battery well of the defibrillator.

Returning to FIG. 3, the back 60 of the battery pack is formed with two sockets 62. Each socket 62 contains a conductive pin 64 that is connected to battery cells located within the battery pack. Preferably, one conductive pin is connected to a positive terminal of the cells within the battery pack, and the other conductive pin is connected to a negative terminal of the cells within the battery pack. Locating the conductive pins on the back 60 of the battery pack opposite the latch 34 minimizes the likelihood that a user will inadvertently come in contact with the conductive pins. The back of the battery pack is also formed with a hole 66 sized to receive a plastic plug 68. The use of the plug to prevent connection of a non-rechargeable battery pack to a battery charger will be discussed in greater detail below.

Figure 5:
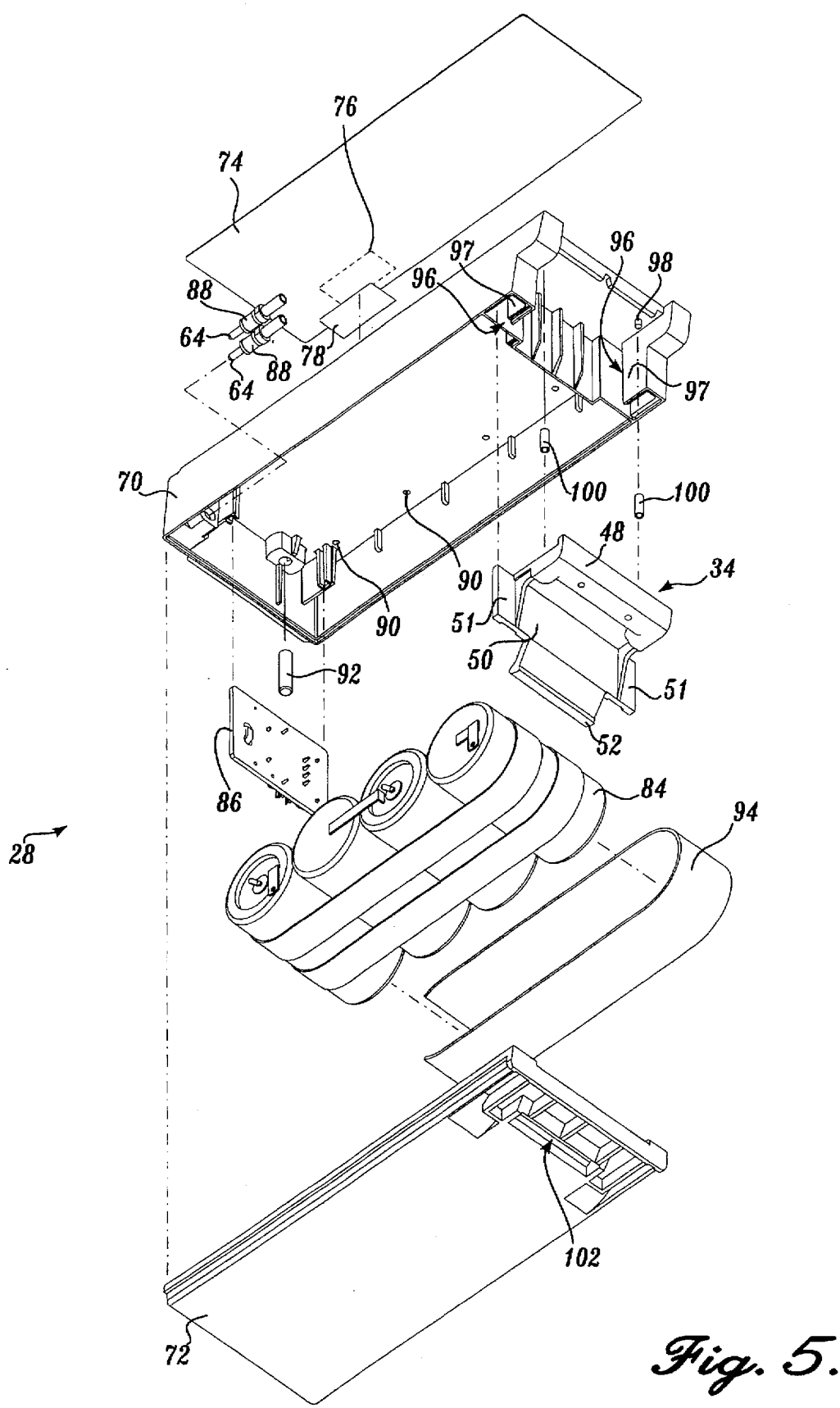
FIG. 5 is an exploded perspective view of the battery pack as viewed from the bottom of the battery pack.

The internal construction of the battery pack will be better appreciated with respect to the exploded view of FIG. 5. As shown in FIG. 5, the case of the battery pack is generally comprised of a cover 70 and a base 72. Preferably cover 70 and base 72 are formed of injection-molded plastic and bonded together by ultrasonic welding. Those skilled in the art will appreciate, however, that the cover and base may be formed of other materials and bonded using a variety of techniques.

A label 74 containing general information identifying the type of battery pack, describing the insertion of the battery pack, and discussing the appropriate disposal of the battery pack is applied to the top of the cover. Label 74 is formed with a clear portion 76 through which a second, and smaller, identification label 78 is viewed. Identification label 78 contains a unique serial number and a date code for each battery pack. The use of identification label 78 allows the battery packs to be tracked during manufacturing and in the field. Identification label 78 is applied to cover 70 prior to application of label 74.

The heart of the battery pack is four cells 84 that are connected in a series with one another. The voltage of each cell is selected to satisfy the power requirements of defibrillator 20. The type of cell is selected depending upon the particular requirements of the user, and environment in which the defibrillator will be used. In one embodiment in the battery pack, cells 84 are non-rechargeable cells, preferably lithium-sulfur dioxide (LiSO$_2$) cells (hereinafter "lithium cells"). Each lithium cell generates three volts, with the series connection of the four lithium cells generating 12 volts. Lithium cells are non-rechargeable, but have a very high energy density. A lithium battery pack will therefore ensure an extended operating time for defibrillator 20. When the lithium cells are nearly discharged, however, the entire battery pack must be discarded.

The cells 84 are connected to a safety circuit contained on a circuit board 86 within the battery pack. Wires (not shown) from the cells connect to two fuses contained on circuit board 86. The first fuse is a current fuse that will trip if sufficient current flows through the fuse. Undue current flow from the cells may be caused by a short within the defibrillator, or a short across the conductive pins 64 on the exterior of the battery pack. The second fuse is a thermal fuse that will trip when the temperature within the battery pack reaches a predetermined threshold. The thermal fuse will therefore trip due to certain types of cell failure within the battery pack, or other environmental condition causing the temperature within the battery pack to unduly rise. Wires (not shown) from the second fuse connect to connectors 88 and connective pins 64 that are fitted within the sockets in the cover 70 of the battery pack. Current therefore flows from the cells to the defibrillator through the safety circuit and the connectors.

If cells 84 are lithium cells, several additional safety features are incorporated in the battery pack. Vent holes 90 are formed in the upper surface of the cover 70. In the event of a cell failure, lithium cells will occasionally vent gases during the failure. To avoid a build up of gases within the battery pack, vent holes 90 are provided to allow the gases to vent to the exterior of the battery pack. Although vent holes 90 are covered by label 74, the pressure of the gases within the battery pack will cause label 74 to peel back from the margins of the label, allowing the gases to escape to the exterior of the battery pack. Before peeling back, however, label 74 maintains the water resistance of the battery pack. Although preferably formed in the upper cover of the battery pack, it will be appreciated that vent holes 90 may be located anywhere on the battery pack case.

When the lithium cells are nearly discharged and the battery pack is to be disposed, it is also desirable to completely drain the charge within the lithium cells. To ensure complete drainage of the lithium cells, a shorting pin 92 is provided in a slot 94 located in the cover 70 of the battery pack. Shorting pin 72 is a conductive pin that is normally flush with the upper surface of the battery pack cover when the battery pack is manufactured. To discharge the battery pack, a screwdriver is placed across the top of the shorting pin 92, with the blade of the screwdriver parallel with the slot 94 formed in the surface of the cover. A sharp blow to the screwdriver will cause the shorting pin 92 to travel in a downward direction. When forced downward in the battery pack, shorting pin 92 bridges two contacts contained in the safety circuit on circuit board 86. Bridging the contacts connects the cells 84 with a resistor on the circuit board 86, dissipating any remaining energy within the cells through the resistor. The battery pack may then be safely disposed of in a landfill since it is completely discharged.

In a second embodiment of the battery pack, cells 84 are rechargeable cells, preferably sealed lead acid (SLA) cells. Each SLA cell generates two volts, with the series connection of the four SLA cells generating eight volts. The energy density of the SLA cells are not as high as lithium cells, therefore the SLA cells will generally power defibrillator 20 for a shorter period of time. SLA cells are, however, rechargeable. A battery pack with SLA cells is therefore periodically connected to a charger in order to recharge the battery pack and allow the battery pack to be reused.

To prevent connection of a charger to the lithium battery pack, in the preferred embodiment plug 68 is permanently inserted into hole 66 on the back of the lithium battery pack. An adapter on a battery charger (not shown) that is designed to connect the battery charger with the sockets 62 on the rear of the battery pack contains three fingers. Two of the fingers fit within sockets 62, establishing an electrical connection between the charger and the cells within the battery pack. The third finger is sized to fit within hole 66. Since hole 66 is filled with plug 68 on the lithium battery pack, it is impossible to connect the battery charger adapter to the lithium battery pack. The plug is absent in a SLA battery pack, allowing the charger to connect to the battery pack and recharge the SLA cells.

If cells 84 are SLA cells, it is not necessary to provide a shorting pin 72 to discharge the remaining energy in the battery pack. The safety circuit within the SLA battery pack still includes, however, a current fuse that will trip in the event of a cell failure or short. Vent holes 90 may also be included in the cover of a SLA battery pack, although venting of SLA cells is much less pronounced than venting of lithium cells.

To prevent the battery cells 84 from shifting in the battery pack, a foam tape 94 is placed around the exterior of the cells. The foam tape compresses as cover 70 is sealed with base 72, firmly securing the cells 84 within the battery pack. The other components contained in the battery pack are held in place by molded structures in the cover 70. The latch 34 is secured between the cover and the base by two molded arms 97 which define two slots 96 in the cover. The body 50 of the latch contains two lateral tabs 51 that extend from the body and fit within the slots 96. When the cover and the base are sealed together, the slots restrict the motion of latch 34 so that the latch can only move upwards and downwards within the slots.

Biasing the latch in an extended position are a pair of coil springs 100 between the latch and the cover. Springs 100 fit over a pair of pegs 98 and abut the cover and the latch handle. When biased downward by the springs, latch member 52 extends through a slot 102 in the base 72 of the battery pack. To raise the latch, a user applies force to move the handle 48 of the latch towards the cover of the battery pack. When raised upwards, the latch member 52 is withdrawn through slot 102 so that it does not protrude below the bottom of the battery pack.

Figure 6:
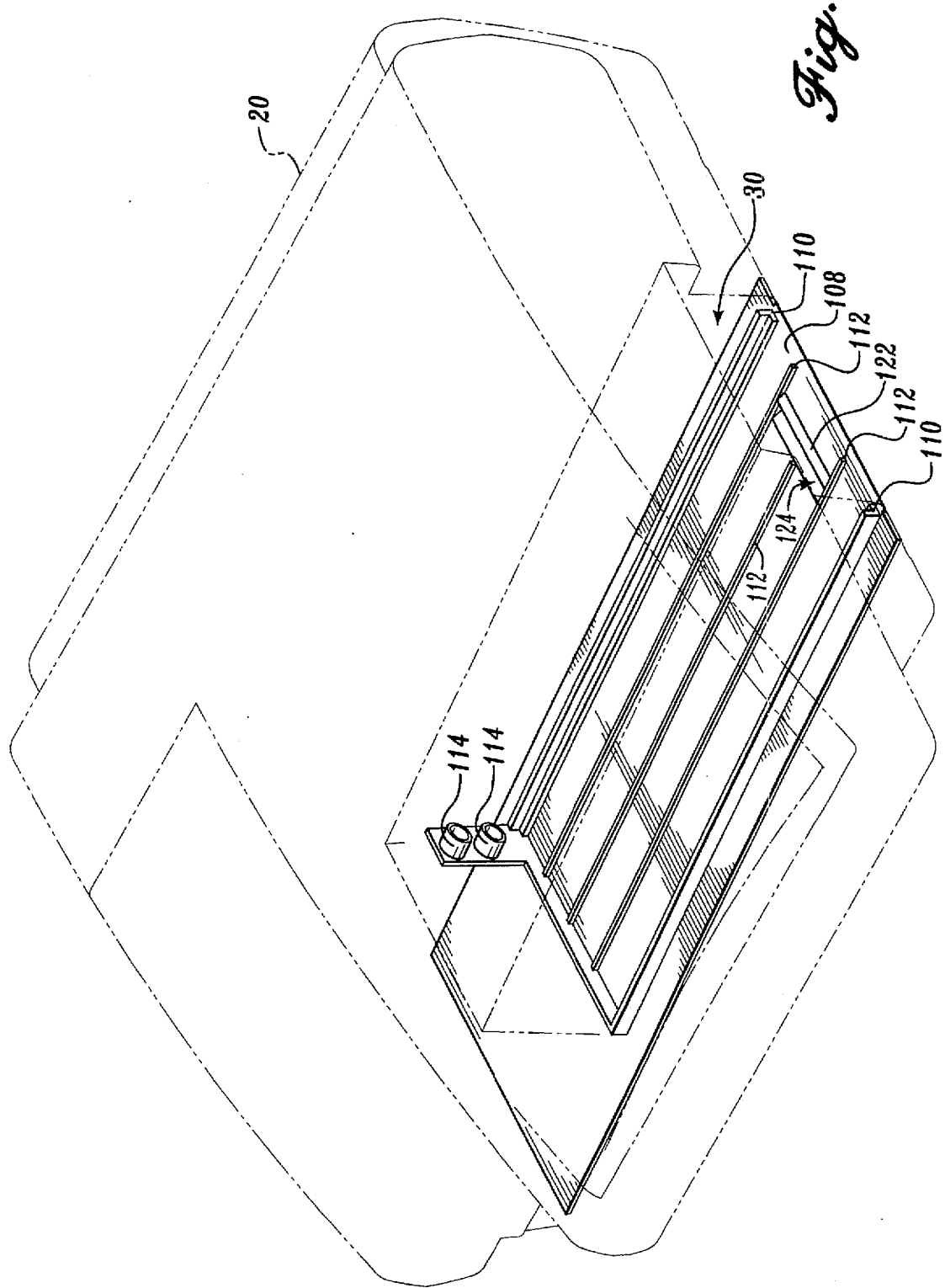
FIG. 6 is a perspective view of a battery well for receiving the battery pack, with the defibrillator shown in phantom view.

The operation of the latch will be greater appreciated with reference to FIG. 6 and FIGS. 7A–C. FIG. 6 depicts the interior of the battery well 30 with the defibrillator 20 shown in phantom view. The floor 108 of the battery well is constructed with two L-shaped guides 110 that extend along the side walls of the battery well, parallel with the path that the battery pack must travel when inserted into the defibrillator. The vertical portion of the guides 110 are sized to fit within in-cut corners 46 constructed in the lower left and right sides of the battery pack. As the battery pack is initially slid into the battery well, the guides correctly align the battery pack. As the battery pack is further slid into battery well, the guides ensure that the battery pack remains properly aligned to mate with the defibrillator.

To reduce the friction between the battery pack and the floor of the battery well, three ridges 112 are provided on the floor. The ridges are generally parallel, and extend from near the entrance of the battery well to the rear wall of the battery well. The ridges support the battery pack as the battery pack is being inserted into the battery well. By raising the battery pack above the flat surface of the battery floor, the ridges prevent the battery pack from getting jammed due to loose debris or other material that may inadvertently accumulate on the battery well floor. As discussed above, the upper surface of the battery pack is constructed with similar ridges that run the length of the battery pack. The ridges on the upper surface of the battery pack prevent the smooth upper surface of the battery pack from coming into contact with the ceiling of the battery well.

In addition to assuring proper alignment of the battery pack as the battery pack is inserted into the battery well, guides 110 also function like the ridges by preventing the smooth side walls of the battery pack from coming into contact with the interior walls of the battery well. The guides 110 keep the battery pack centered within the battery well so that there is a slight gap between the left and right walls of the battery pack and the interior walls of the battery well. It will be appreciated that the addition of guides 110 and ridges 112 in the battery well, as well as ridge 38 on the battery pack, greatly improves the ease with which the battery pack is inserted and removed from the defibrillator. The battery pack and defibrillator are designed so that inserting or removing the battery pack is a single-handed operation.

When the battery pack is nearly fully inserted into the battery well, two non-conductive sheaths 114 at the rear of the battery well are received by the sockets 62 in the back of the battery pack. Each of the sheaths contains a conductive socket that is designed to mate with the conductive pin 64 in the battery pack. Prior to an electrical connection being made between the conductive pins 64 and the conductive sockets in the sheaths, the sheaths 114 begin to enter sockets 62 on the battery pack. The non-conductive sheaths thereby prevent shorting between the conductive pins located on the battery pack because they shield the pins as the connection is made. When the battery pack is fully inserted into the battery well, an electrical connection is completed between the cells within the battery pack and the electronic circuitry in the defibrillator.

The construction of the battery well and the battery pack ensure that the mating of the conductive pins and the conductive sockets is automatically performed as the battery pack is inserted into the battery well, without requiring the user to align the battery pack. The alignment provided by the guides 110 ensures that the pins on the battery pack will not be broken or bent as the battery pack is inserted into the defibrillator. The disclosed construction is therefore advantageous for a first responder defibrillator since it minimizes the necessary skill to change the battery pack.

Figure 7A:
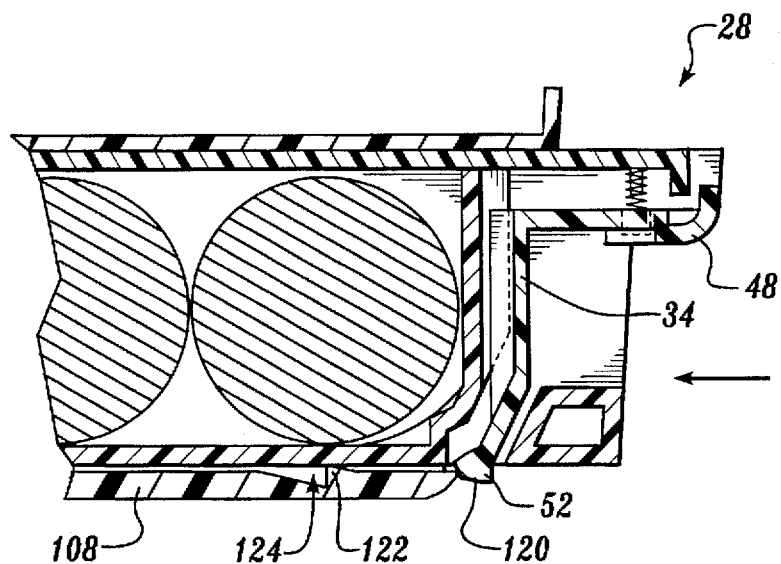
FIGS. 7A–C are cross-sections of the battery pack and battery well, depicting operation of the latch to secure the battery pack in the battery well.
Figure 7B:
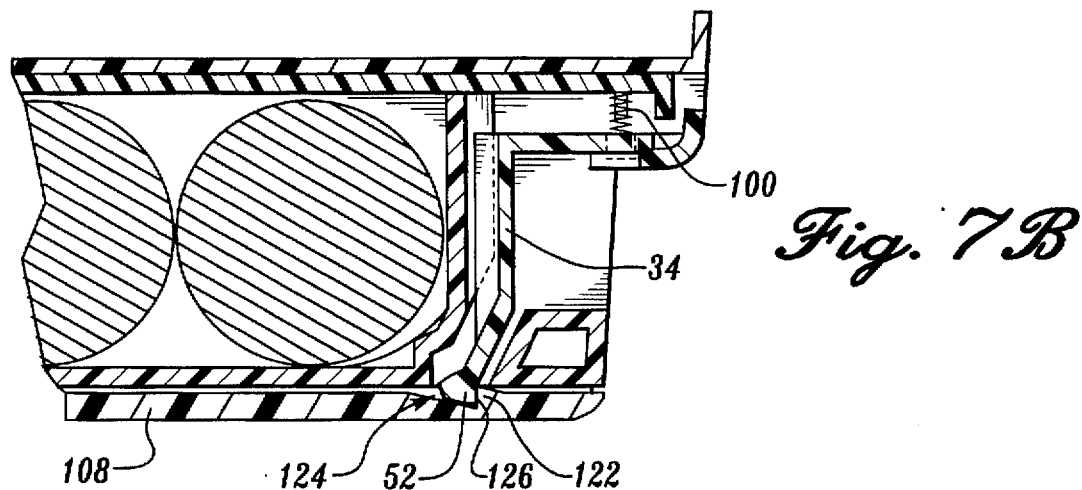
Figure 7C:
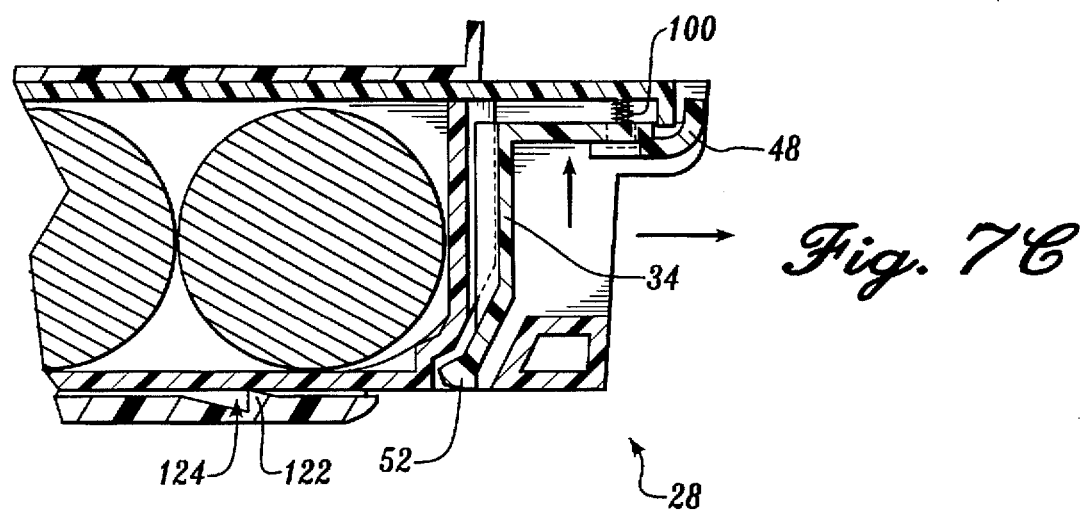

To prevent the battery pack from falling out of the battery well once it has been inserted, latch 38 is designed to automatically secure the battery pack in the battery well. FIGS. 7A–C depict the position of the latch as the battery pack is being inserted and removed from the defibrillator. In FIG. 7A, the battery pack is being inserted into the battery well. As the battery pack is slid into the battery well, a leading face 120 of the latch member 52 comes into contact with the front lip of the floor 108 of the battery well. The leading face 120 of the latch member is angled so that as the battery pack is further inserted into the battery well, the latch member is automatically forced upward as the leading face contacts the front lip. A user therefore does not have to move latch 34 when inserting the battery pack, since the raising of the latch member 52 is automatically performed.

In FIG. 7B, the battery pack has been fully inserted into the defibrillator. As the battery pack nears the position shown in FIG. 7B, the latch member 52 travels up a ramp 122 that is formed in the floor 108 of the battery well. Again, the angled leading face of the latch member causes the latch to move further upward as the latch member travels up the ramp. After traveling over the ramp, the latch member is forced into a slot 124 by the biasing action of springs 100 on the latch 38. A trailing face 126 of the latch member is generally flat. When the latch member is captured in slot 124, the trailing face of the latch member is brought into contact with the flat backside of ramp 122. The contact between the latch member and the ramp secures the battery pack in place, and prevents the battery pack from becoming separated from the defibrillator.

To remove the battery pack, a user must apply an upward force to the latch to retract the latch member from the slot.

FIG. 7C depicts the necessary movement of the latch 34 in order to remove the battery pack from the battery well. To remove the latch member 52 from the slot 124, the user must lift handle 48 to compress springs 100. Lifting the handle raises the latch member so that the trailing face of the latch member clears the flat backside of ramp 122. As the handle is raised, the user must also apply an outward force to slide the battery pack 28 from the battery well. Once the latch member clears the ramp, the user may return the latch to the extended position.

It will be appreciated that the disclosed latch construction greatly facilitates the insertion of the battery pack during an emergency. To insert the battery pack, the user must merely align the battery pack with the entrance of the battery well, and insert the battery pack until the latch automatically latches into the slot in the battery well. The self-latching latch speeds the insertion process and prevents the battery pack from becoming detached from the defibrillator.

While the preferred embodiment of the invention has been illustrated and described, it will be appreciated that various changes can be made therein without departing from the spirit and scope of the invention. For example, while a ridge is preferably incorporated on the top of the battery pack, it will be appreciated that the ridge could alternately be constructed in the ceiling of the battery well. Moving the ridge to the ceiling of the battery well would achieve the desired result of reducing the friction between the battery pack and the battery well as the battery pack is being inserted in the defibrillator.

Those skilled in the art will also appreciate that alternate structures could be used to bias the latch in an extended position. A pair of coil springs 100 are preferably used to apply a force to latch 38. Other compressible structures, including a leaf spring and rubber grommets, could also be used to apply a similar force to the latch.

Those skilled in the art will further appreciate that various types and numbers of cells 84 could be used in the battery pack construction disclosed herein. Other types of rechargeable and non-rechargeable cells may be incorporated in the battery pack, depending on the preference of the user and the expected operating environment. The number of cells could also be varied, depending on the required operating voltage of the defibrillator. In certain environments, only a single cell may be required in the battery pack.

It will also be appreciated that the asymmetric shape of the battery pack could be varied other than the preferred shape disclosed herein. Rather than only one of the walls being inclined from vertical, both the left and right walls 42, 44 of the battery pack may be inclined from vertical. The inclination angle for each wall must, however, be different to ensure an asymmetric shape for keying purposes. Consequently, within the scope of the appended claims, it will be appreciated that the invention can be practiced otherwise than as specifically described herein.

The embodiments of the invention in which an exclusive property or privilege is claimed are defined as follows:

1. A battery pack for use in a portable defibrillator having a battery well, the battery pack comprising:
   (a) a parallelepiped body having a front and a back;
   (b) a cell having a positive terminal and a negative terminal contained within the body;
   (c) a pair of conductive contacts located on the back of the body, one of the pair of conductive contacts coupled to the positive terminal of the cell and the other of the pair of conductive contacts coupled to the negative terminal of the cell;
   (d) a latch located on the front of the body, the latch having a latch member that is movable between an extended position wherein the latch member protrudes from the body, and a retracted position wherein the latch member does not protrude from the body; and
   (e) biasing means to bias the latch member in the extended position, wherein partial insertion of the battery pack into the battery well causes the latch member to move to the retracted position, the biasing means returning the latch member to the extended position after the battery pack is fully inserted in the battery well in order to secure the battery pack in the battery well of the defibrillator.

2. The battery pack of claim 1, wherein the latch member has an angled leading face oriented in a direction of battery pack insertion, and a trailing face oriented away from the direction of battery pack insertion.

3. The battery pack of claim 2, wherein the leading face of the latch member contacts a wall of the battery well and moves the latch member to the retracted position when the battery pack is partially inserted into the battery well.

4. The battery pack of claim 1, wherein the latch includes a latch handle that is graspable by a user to manually move the latch member to the retracted position.

* * * * *

UNITED STATES PATENT AND TRADEMARK OFFICE
CERTIFICATE OF CORRECTION

PATENT NO.  : 5,741,305
DATED       : April 21, 1998
INVENTOR(S) : S.T. Vincent et al.

It is certified that error appears in the above-identified patent and that said Letters Patent is hereby corrected as shown below:

On the title page, Item [56]
    Please insert the following references:
        --349,483      8/1994    Weaver et al.
          295,739      5/1988    Lanci et al.
        4,590,943      5/1986    Paull et al.--

Signed and Sealed this

First Day of September, 1998

Attest:

BRUCE LEHMAN

Attesting Officer

Commissioner of Patents and Trademarks